United States Patent [19]
Crawford et al.

[11] Patent Number: 5,370,998
[45] Date of Patent: Dec. 6, 1994

[54] REPETITIVE DNA SEQUENCE SPECIFIC FOR MYCOBACTERIUM TUBERCULOSIS TO BE USED FOR THE DIAGNOSIS OF TUBERCULOSIS

[75] Inventors: Jack T. Crawford, Atlanta, Ga.; Kathleen D. Eisenach, Little Rock, Ark.; M. Donald Cave, Little Rock, Ark.; Joseph H. Bates, Little Rock, Ark.

[73] Assignee: The Board of Trustees of The University of Arkansas, Little Rock, Ark.

[21] Appl. No.: 769,233

[22] Filed: Oct. 1, 1991

Related U.S. Application Data
[62] Division of Ser. No. 589,819, Sep. 28, 1990.

[51] Int. Cl.$^5$ ............................................. C12P 19/34
[52] U.S. Cl. ........................................ 435/91.2; 435/6; 536/24.3; 935/78
[58] Field of Search ............... 435/6, 91.2; 536/24.3; 935/78

[56] References Cited

U.S. PATENT DOCUMENTS

| | | | |
|---|---|---|---|
| 4,358,535 | 11/1982 | Falkow et al. | 435/5 |
| 4,683,202 | 7/1987 | Mullis | 435/91 |
| 4,725,536 | 2/1988 | Fritsch et al. | |
| 4,755,458 | 7/1988 | Rabbani et al. | |
| 4,831,125 | 5/1989 | Saltzgaber-Muller | |
| 4,886,743 | 12/1989 | Hood et al. | |
| 4,918,178 | 4/1990 | Hurley et al. | |

FOREIGN PATENT DOCUMENTS

| | | |
|---|---|---|
| 0288306 | 10/1988 | European Pat. Off. |
| 2651505 | 3/1991 | France |
| 3-164199 | 7/1991 | Japan |
| WO91/03558 | 9/1990 | WIPO |

OTHER PUBLICATIONS

Maniatis et al., "Molecular Cloning A Laboratory Manual", 1982, pp. 366–369, Cold Spring Harbor Laboratory.

Eisenach et al., Polymerase Chain Reaction Amplification of a Repetitive DNA Sequence Specific for Mycobacterium Tuberculosis Journal of Infectious Diseases, vol. 161, 1990, pp. 977–981.

Eisenach et al., Repetitive DNA Sequences as Probes for Mycobacterium Tuberculosis, Journal of Clinical Microbiology, vol. 26, No. 11, Nov. 1988, pp. 2240–2245.

Eisenach et al., Genetic Relatedness Among Strains of the Mycobacterium Tuberculosis Comples, American Review of Respiratory Disease, vol. 133, 1986, pp. 1065–1068.

Thierry et al., IS6110, an IS-like Element of Mycobacterium Tuberculosis Complex, Nucleic Acids Research vol. 18, No. 1 1990, p. 188.

*Primary Examiner*—Amelia Burgess Yarbrough
*Attorney, Agent, or Firm*—Hermann Ivester

[57] ABSTRACT

A novel composition and/or methods for the diagnosis of tuberculosis wherein the composition comprises a repetitive DNA segment that is specific for members of the *Mycobacterium tuberculosis* complex. The DNA segment repeats in the chromosome of *Mycobacterium tuberculosis* complex, and is conserved in all copies of the chromosomes. A method comprises using an entire repetitive DNA sequence, or any part thereof, as a hybridization probe for the direct detection of *Mycobacterium tuberculosis* complex in clinical material. In another method, a smaller portion of an entire repetitive DNA sequence is amplified using polymerase chain reaction, yielding a 123 base-pair product.

19 Claims, 1 Drawing Sheet

REPETITIVE DNA SEQUENCE SPECIFIC FOR MYCOBACTERIUM TUBERCULOSIS TO BE USED FOR THE DIAGNOSIS OF TUBERCULOSIS

This is a division, of application Ser. No. 589,819, filed Sep. 28, 1990.

FIELD OF THE INVENTION

The present invention relates to a specific DNA sequence. More precisely, the present invention relates to a composition comprising a specific DNA sequence that is unique to a pathogenic microorganism. The present invention further relates to the utilization of the composition to detect the pathogenic microorganism in clinical material.

BACKGROUND OF THE INVENTION

Tuberculosis, an infectious disease caused by the microorganism *Mycobacterium tuberculosis*, continues to remain a major global health problem. In the United States, tuberculosis still persists as a significant health problem, particularly in underprivileged and minority populations, among immigrants from high-risk countries, and in other high-risk groups, such as individuals with human immunodeficiency viral infections.

A definitive diagnosis of tuberculosis depends upon the isolation of *Mycobacterium tuberculosis* (sometimes referred to hereinafter as "*M. tuberculosis*") from the secretions or tissues of an infected individual in conjunction with clinical findings of the disease. Because of the length of time required for isolation of *M. tuberculosis* and the subsequent diagnosis of tuberculosis, a longstanding goal of researchers has been to develop a rapid, sensitive, and specific test for the detection of the organism in clinical specimens. Such a test could substantially decrease the time required to definitively diagnose tuberculosis, and assist the health care provider in administering the appropriate therapeutic treatment.

A variety of methods have been used for detection of *M. tuberculosis*. With culture identification procedures, a specimen is typically placed on an acceptable culture medium, incubated at a specific temperature for a period of time, and then inspected for growth of the organism. Although routinely performed, these procedures are highly technical, expensive, and laborious.

A second method, direct microscopy, involves the direct examination of smears prepared from a clinical specimen. Although the most rapid method for detecting mycobacteria, direct microscopy is limiting because technical expertise is required in interpreting smears and a large number of bacteria must be present for detection.

Non-cultural methods, such as radioimmunoassay, latex agglutination and enzyme immunosorbent assay, have also been employed for the direct detection of *M. tuberculosis*. These approaches appear to be promising because of their rapidity. However, a major limitation with these methods is the lack of sensitivity in detecting the organism.

A more promising diagnostic approach has been achieved with recombinant DNA and hybridization techniques. Nucleic acid hybridization assays have been used to detect and identify target genetic materials such as DNA in clinical specimens. See Tenover, Clin. Microbiol. Rev. 1: 82–101, 1988. The assay is premised upon the presence of a specific nucleotide sequence in the target genetic material, and the detection of this sequence. The direct detection of the specific nucleotide sequence actually occurs by use of a nucleic acid probe. A probe is a nucleotide sequence that is complementary to the DNA sequence of one of the strands of the DNA molecule that is desired to be detected in the clinical sample. A detectable marker is attached to the probe.

DNA probe technology offers advantages over other detection methods. The detection time is shorter, and the technology is not dependent upon the viability of the organism. Despite these benefits, a significant limitation of this technology is its lack of sensitivity in detecting *M. tuberculosis*.

A DNA probe system is available for detecting species of mycobacteria, but only after the organism has grown in culture (Gen-Probe, Inc.). Gonzalez et al., Diagn. Microbiol. Infect. Dis., 8: 69–77, 1987. However, no direct probe for the detection of mycobacteria in clinical specimens is currently available.

SUMMARY OF THE INVENTION

The present invention provides a composition that comprises a repetitive DNA segment that is specific for members of the *Mycobacterium tuberculosis* complex (e.g., *M. tuberculosis*, *M. bovis*, and *M. bovis* BCG). The DNA segment can be used as a hybridization probe and as a target of amplification for the direct detection of the DNA from the *Mycobacterium tuberculosis* complex in clinical material.

In one embodiment of the present invention, the composition comprising a DNA segment repeats in the chromosome of *M. tuberculosis*.

In another embodiment, the nucleotide sequence of the DNA segment is conserved in all copies of the chromosomes of *M. tuberculosis* complex.

In an embodiment, the repetitive DNA segment is present in clones, λKE55 and λKE58.

In another embodiment of the present invention, a portion of the repetitive DNA segment in *M. tuberculosis* is used as target material for amplification by polymerase chain reactions, wherein amplification produces a 123 base-pair product.

In a further embodiment, a repetitive DNA segment in *M. tuberculosis* is used as a hybridization probe for directly detecting isolates of the *M. tuberculosis* complex in clinical material.

Additional features and advantages of the present invention are further described, and will be apparent from the detailed description from the presently preferred embodiments.

DETAILED DESCRIPTION OF THE PRESENTLY PREFERRED EMBODIMENTS

Figure 1:
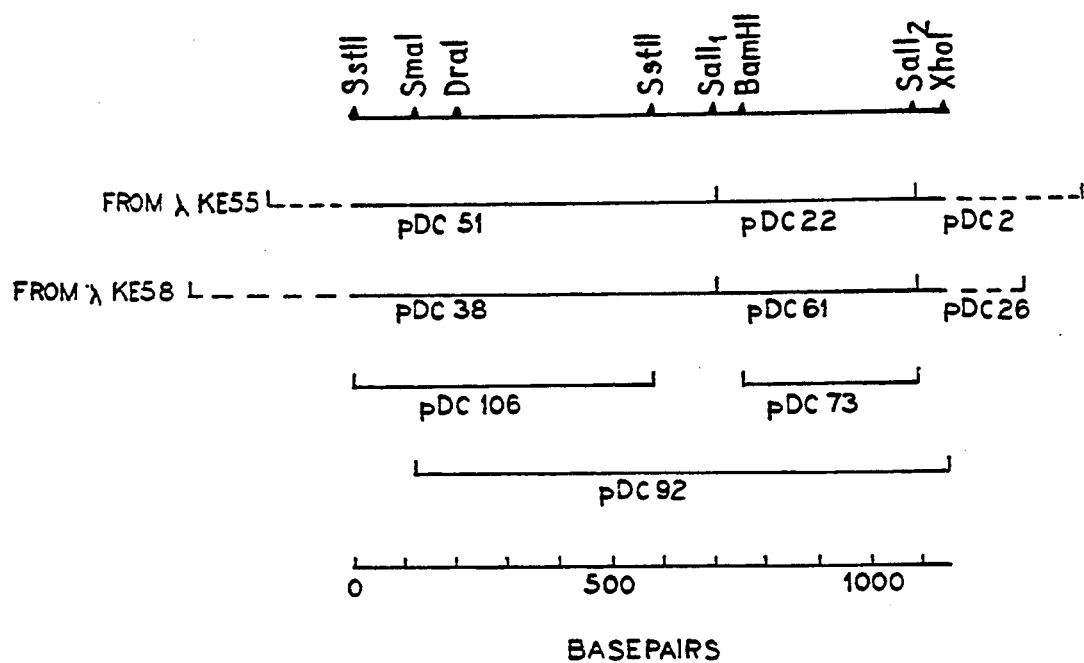
FIG. 1 illustrates a restriction map of λKE55 and λKE58, clones isolated from a lambda phage library of *Mycobacterium tuberculosis* DNA. The map is based on restriction digests of the plasmid subclones illustrated. Contiguous and overlapping regions are shown.

The present invention pertains to a composition comprising a repetitive segment of *Mycobacterium tuberculosis* DNA that has been isolated, cloned, restriction mapped, and partially sequenced. The present invention further contemplates the usefulness of this segment as a diagnostic tool in detecting the presence of *M. tuberculosis* in clinical material.

Pursuant to the present invention, *M. tuberculosis* DNA segments were isolated in purified form, inserted into a bacteriophage vector, followed by transfection of appropriate host cells. The resulting recombinants or clones were radiolabeled and screened for use as *M. tuberculosis*-specific nucleotide probes. To this end, Southern and slot blots containing purified DNA from representative strains of the *M. tuberculosis* complex were hybridized with the labeled DNA of the recombinants. Representative strains of the *M. tuberculosis* complex include *M. tuberculosis* H37Rv, *M. tuberculosis* H37Ra, *M. bovis*, and clinical isolates of *M. tuberculosis*.

As will be shown in the following examples, three cloned DNA segments of *M. tuberculosis* hybridized with multiple chromosomal fragments of *M. tuberculosis* complex, indicating the repetitive nature of the DNA segments. Specifically, each segment was found to repeat in the range of 10–16 times in the *M. tuberculosis* chromosome.

Since one of these cloned DNA segments represented only a small portion of the entire repetitive sequence, additional cloning was performed to isolate the complete repetitive segment. A lambda phage library was established and two clones, λKE55 and λKE58, were found to contain the repetitive DNA fragment. The fragments of these 2 clones were subcloned, and the subclones were subsequently mapped with restriction endonucleases.

Subsequent studies revealed that the repetitive DNA segment was conserved in multiples copies in the chromosomes of individual strains of *M. tuberculosis* complex. Further, the hybridization assays demonstrated the specificity of the repetitive segment for strains of the *M. tuberculosis* complex.

Additional studies demonstrated the various uses of the repetitive DNA segment as a hybridization probe. Examples include direct detection of *M. tuberculosis* in clinical samples, culture confirmation of isolated strains, and chromosomal fingerprinting methods.

A representative portion of the repetitive DNA segment in *M. tuberculosis* was subsequently sequenced. A 123 base-pair segment was selected as a target for amplification using polymerase chain reactions, sometimes referred to hereinafter as "PCR". Amplification of the segment using PCR demonstrated the presence of a 123 base-pair segment in the chromosome of *M. tuberculosis*, and was specific for DNA from *M. tuberculosis* complex strains. Further, the sensitivity of detection by amplifying *M. tuberculosis* DNA may provide the basis for an assay to detect the organism directly in clinical material.

By way of example, and not limitation, the following examples serve to further illustrate the present invention in its preferred embodiments.

EXAMPLE 1

(1) Materials

Clinical isolates of *M. tuberculosis* and *M. kansasii* were obtained from the microbiology laboratories of McClellan Memorial Veterans Hospital and Baptist Medical Center, Little Rock, Ark. *M. avium* strains LR541, 542, 551, 552, 588, and 593 were AIDS-associated isolates obtained from the Centers for Disease Control, Atlanta, Ga. All other strains were obtained from the reference laboratories at National Jewish Center for Immunology and Respiratory Medicine, Denver, Colo. The strains used are listed in Table 1.

TABLE 1

| Mycobacterial strains | | |
|---|---|---|
| Organism, strain serotype | Organism, strain | Organism, strain, serotype |
| *M. tuberculosis* | *M. kansasii* | *M. avium* complex |
| Clinical T2 | TMC1204 | LR147.1 |
| H37Rv (TMC102) | TMC1217 | LR588.1 |
| H37Ra Goldman | Clinical K4 | LR593.1 |
| Clinical T1 | Clinical K5 | LR113.4 |
| Clinical T3 | Other | LR541.4 |
| Clinical T4 | *M. fortuitum* TMC1530 | LR542.4 |
| Clinical T5 | *M. simiae* TMC1226 | LR150.8 |
| Clinical T6 | *M. gordonae* TMC1324 | LR551.8 |
| *M. bovis* | *M. chelonei* TMC1543 | LR552.8 |
| TMC401 | | TMC715.2 |
| TMC410 | | LR107.3 |
| BCG Glaxo (TMC1024) | | LR163.6 |
| *M. scrofulaceum* | | TMC1479.9 |
| TMC1315.41 | | LR158.10 |
| TMC1309.42 | | LR105.11 |
| LR121.43 | | TMC1466.13 |
| | | LR127.19 |
| | | LR141.26 |

(2) Preparation of Mycobacterial DNA

In order to isolate the DNA sequence that is specific for *M. tuberculosis*, the DNA must be separated from the rest of the cell. To accomplish this, cells were cultured in 100 ml of Middlebrook 7H9 broth (Difco Laboratories) containing 0.05% Tween 80 in 500 ml baffled side-arm flasks. Cultures were incubated at 37° C. on a rotary shaker. A Klett colorimeter was used to monitor the cell density. When the cultures were in log phase, D-cycloserine was added to a final concentration of one mg/ml. Cultures were reincubated until the density decreased slightly, which usually occurred within 48 to 72 hours. Cells were harvested by centrifugation, washed once with: STE, and suspended in 2 ml of lysis buffer containing 15% sucrose, 0.05M TRIS-hydrochloride (pH 8.5), and 0.05M EDTA. Lysozyme was added (1 mg/ml), and the cell suspension was incubated for 30 minutes at 37° C. Proteinase K was added (0.1 mg/ml), and the suspension was incubated at 25° C. for 10 minutes.

Sodium dodecyl sulfate (SDS), a lysing agent, was added to a final concentration of 1%. Addition of the lysing agent resulted in the *M. tuberculosis* chromosomal DNA being accessible for subsequent purification. For purification of the organism's chromosomal DNA, the DNA was extracted twice with phenol-chloroform-isoamyl alcohol, purified by dialysis, and concentrated by ethanol precipitation. The DNA concentration was determined by optical density at 260 nm.

The purified chromosomal DNA was then digested into fragments with a restriction endonuclease. Reaction mixtures contained 1 to 2 μg of DNA and 4 to 10 U of enzyme. Digest conditions were specified by the manufacturer of the enzyme (Bethesda Research Laboratory, Inc. or New England BioLabs, Inc.). To verify that the digestion had proceeded sufficiently for cloning, agarose gel electrophoresis was utilized to measure the size of the DNA fragments.

(3) Cloning

Each of the chromosomal DNA fragments was then inserted into a vector (e.g. bacteriophage) to form a recombinant molecule. To accomplish this, DNA from a clinical isolate of *M. tuberculosis*, designated T2, was digested with Mbol and ligated with a BamH1 digest of M13mp18 replicative form. The recombinant molecule was then transfected into *Escherichia coli* JM101 cells and plated. The recombinants, which appeared as colorless plaques, were picked to freshly seeded agar plates. Duplicate plaque lifts were made from each plate.

Recombinant phage were propagated in log-phase cultures of *E. coli* JM101. The single-stranded DNA was isolated from culture supernatants by polyethylene glycol precipitation. Double-stranded (replicative form) DNA was isolated from cell pellets by alkaline lysis method. To excise the insert DNA, the replicative-form DNA was digested with EcoR1 and Hind 111. The sizes of the excised fragments were determined by agarose gel electrophoresis.

(4) Labeling DNA Probes

To radiolabel the DNA probe, the DNA was labeled with [$\alpha$-$^{32}$P]dCTP by nick translation. Single-stranded M13 DNA was labeled with $^{32}$P by primer extension, using the procedure of Hu and Messing (Gene 17:271-277, 1982). Specific activity of the probe was about $10^8$ cpm/$\mu$g of DNA, and approximately $10^6$ to $10^7$ cpm was used in each hybridization.

(5) Slot Blot Hybridizations

To assess the potential of these recombinants for use as *M. tuberculosis*-specific probes, slot blot hybridizations were performed. Slot blots containing 128 ng of purified DNA from representative strains of the *M. tuberculosis* complex (*M. tuberculosis* H37Rv, *M. tuberculosis* H37Ra, *M bovis*, and clinical isolates of *M. tuberculosis*) were hybridized with the labeled single-stranded form of the recombinants. To accomplish this, purified DNA was denatured in 0.4N NaOH at room temperature for 10 minutes, neutralized with an equal volume of 2M ammonium acetate (pH 7), and then loaded on a slot blotter (Minifold II; Schleicher and Schuell, Inc.) containing a BA85 nitrocellulose membrane. Next, fixing of the DNA to the membrane was done to prevent the DNA from being washed off the membrane during the subsequent hybridization/wash step. Fixing was carried out by placing the membranes in a vacuum oven at 80° C.

The DNA was then blocked to prevent any nonspecific binding to the membrane by the recombinant DNA and the labeled probe. Blocking was carried out by incubating the membrane in a standard hybridization solution consisting of 6×SSC (0.9M NaCl plus 0.09M sodium citrate), 5×Denhardt solution and 100 $\mu$g of denatured salmon sperm DNA per ml. EDTA (0.01M) and labeled probe DNA were added to the hybridization solution. Membranes were hybridized over night at 68° C. and then washed as follows: 2×SSC in 0.5% SDS at room temperature for 5 minutes, 2×SSC and 0.1% SDS at room temperature for 10 minutes, and 0.1×SSC and 0.5% SDS at 68° C. for 2.5 hours.

Membranes were exposed for variable lengths of time at −70° C. to x-ray film to detect blots where the $^{32}$P-labeled DNA hybridized to *M. tuberculosis* complex DNA.

With the slot blot hybridizations, three recombinants, designated M13KE37, M13KE49, and M13KE115, hybridized strongly with all strains and appeared to be good candidates for clinical probes. To access specificity, slot blots of DNA from mycobacteria commonly found in sputum were hybridized with these three probes. No significant hybridization occurred with the DNA from clinical isolates and reference strains of *M. kansasii* or with reference strains of *M. fortuitum, M. chelonei, M. gordonae* and *M. simiae*. Further, no significant hybridization was detected with clinical and reference strains of *M. avium* serotypes 1, 4, and 8 or with other reference strains representative of this species. When slot blots containing two-fold dilutions of M. tuberculosis DNA were hybridized with these probes, 2 to 4 ng of DNA was detected.

(6) Southern Blot Hybridizations

Another procedure, Southern blot hybridizations, was also used to ascertain more specific information. The M13 recombinants, as previously described, were hybridized with membranes containing BamH1 digests of DNA from members of the tuberculosis complex. Digests were electrophoresed on 0.8% agarose gels containing ethidium bromide and photographed.

The DNA fragments were denatured and transferred to a GeneScreen Plus membrane (DuPont, NEN Research Products) by using either a modified Southern transfer method as described by Maniatis et al., (*Molecular Cloning: A Laboratory Manual.* Cold Spring Harbor Laboratory, Cold Spring Harbor, N.Y., 1982) or the alkaline transfer method of Chomczynski and Qasba (Biochem. Biophys. Res. Commun. 122: 340-344, 1984). GeneScreen Plus was hybridized according to the manufacturer's instructions, except that hybridization was performed at 68° C. without dextran sulfate. The membranes were washed twice with 2×SSC at room temperature for 5 minutes, twice with 2×SSC and 0.1% SDS at 68° C. for 30 minutes, and twice with 0.1×SSC at room temperature for 30 minutes. The membranes were then exposed for various lengths of time to x-ray film at −70° C.

Most notably, all three recombinants hybridized strongly with multiple DNA fragments of *M. tuberculosis*. M13KE37 hybridized strongly with 16 BamH1 fragments of T2 DNA and with 12 fragments of H37Rv. Further, M13KE37 hybridized with nine fragments in the *M. tuberculosis* T1 digest (another clinical isolate) and with five in the *M. bovis* digest. The fragments ranged from 18 to 1 kilobase pairs, indicating a repetitive sequence in the DNA of strains of the *M. tuberculosis* complex. However, the results also suggest that this sequence does not occur with the same frequency in all strains.

A second recombinant, M13KE49, hybridized with 10 BamH1 fragments in the digests of T2 DNA. Similarities in band patterns among the *M. tuberculosis* complex strains indicate that the DNA segment is conserved among the complex strains.

Similarly, M13KE115 hybridized strongly with nine fragments in the T2 digest and less with seven others. The band patterns of all the complex strains were almost identical, indicating that the sequence is highly conserved in all the strains. Further, the three recombinants did not hybridize to a significant extent with DNA from non-tuberculous mycobacteria.

The repetitive DNA segments, as observed among three cloned DNA segments of *M. tuberculosis*, should be useful in enhancing the sensitivity of detection for *M. tuberculosis* in clinical material by a factor of 10-16 as compared to a DNA segment that occurs only once in the chromosome. As a clinical probe in a direct hybridization assay, a repetitive segment could effectively shorten the time for diagnosing tuberculosis in clinical materials.

Additional studies were conducted with M13KE37 to isolate and characterize the complete repetitive sequence of the DNA segment from *Mycobacterium tuberculosis*. In addition, a portion of the DNA segment was selected as a target for amplification by polymerase chain reaction (PCR), a technique that greatly enhances the sensitivity of detection of specific DNA sequences.

EXAMPLE 2

1. Isolation of Subclones Containing the Repetitive Element

Since the repetitive fragment in M13KE37 is only a small portion of a larger repetitive sequence and contains fragments of nonrepetitive DNA, the following approach was used to isolate the complete repetitive segment. A lambda phage library of *M. tuberculosis* DNA was established by cloning a partial EcoR1 digest of strain T2 into the EcoR1 site of the bacteriophage lambda EMBL3 (Frishauf AM, Lebrach H, Poustka A, Murray N. J Mol Biol 170:826, 1983). The phage were grown on *E. coli* strain Q359. Recombinant phage were identified by hybridizing plaque lifts with $^{32}$P-labeled M13KE37. Two of the clones which were isolated from the library, λKE55 and λKE58, were found to contain 400-bp Sal1 fragments which were found to hybridize with one another, and 2 flanking Sal1 sequences which partially hybridized one to another. These fragments of λKE55 and λKE58 were subcloned into the Sal1 site of pUC19 (Yanisch-Perron C, Vieria J, and Messing J. Gene 33:103, 1985). The subclones were designated pDC51 (λKE55), pDC38 (λKE58), pDC22 (λKE55), pDC61 (λKE58), pDC2 (λKE55), pDC26 (λKE58), pDC106 (pDC51), pDC73 (pDC22), and pDC92 (λKE55).

2. Restriction Enzyme Mapping of Subclones

The subclones were mapped with restriction endonucleases to verify common segments, that is fragments which share the repetitive element. As illustrated in FIG. 1, common sites for Sst11, Sma1, and Dra1 were found in pDC51 and pDC38. A common BamH1 site was found in pDC22 and pDC61, and a common site for Xho1 is found in pDC2 and pDC26. Useful additional clones include pDC106, pDC73, and pDC92, which contain various portions of the repetitive sequence which have been used as hybridization probes. While 2 of the Sal1 clones (pDC22 and pDC16) contain a 400-bp Sal1 fragment of the repetitive unit, the other 4 clones (pDC51, pDC2, pDC38, pDC26) contain in addition to the repetitive element nonrepetitive flanking sequences.

Figure 2:
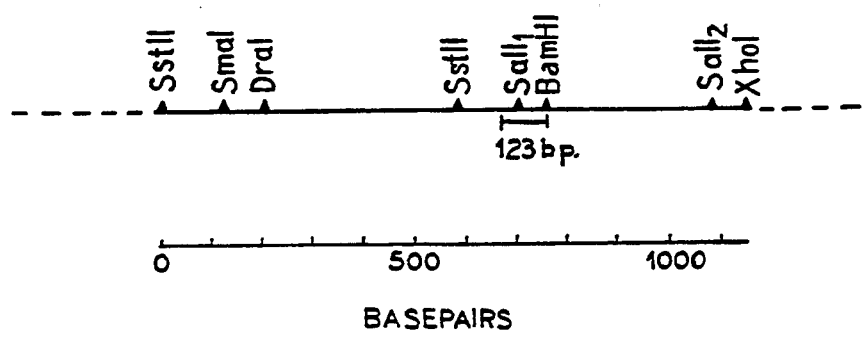
FIG. 2 illustrates a restriction endonuclease map of the repetitive DNA segment in *Mycobacterium tuberculosis*. The segment was derived from digests of the 3 contiguous cloned Sal1 fragments found in λKE55 and λKE58. The location of the DNA sequence, which was selected as a target for amplification using polymerase chain reactions, is also shown.

A restriction endonuclease map of the repetitive element was derived from digests of the 3 contiguous cloned Sal1 fragments found in λKE55 and λKE58. The location of the DNA sequence, which was selected as a target for amplification using PCR, is shown in FIG. 2.

3. Conservation of the Repetitive Element

The question addressed herein was whether all of the copies found in the DNA of a single strain and in various strains of *M. tuberculosis* and *M. bovis* are identical. To this end, genomic DNA from *M. tuberculosis* strains H37Rv, H37Ra Goldman, six clinical isolates, and three strains of *M. bovis* were restricted with enzymes that cleave within the insertion sequence, electrophoresed, blotted, and probed with $^{32}$P-labeled Sal1-BamH1 or Sst11 fragments. A single fragment of identical size (600 bp) was detected by hybridization in all strains, indicating conservation of the Sst11 sites in all copies of the repeat in all strains tested. Similarly, single bands of a size consistent with the restriction map were detected in all strains in which the DNA was digested with Sal1 (400 bp) and combinations of Xho1 and Sma1 (1 Kb), Xho1 and BamH1 (400 bp), and Dra1 and Xho1 (950 bp).

The data demonstrated that 8 restriction sites for 6 restriction endonucleases are conserved within multiple copies of the repetitive element in a single strain, across strain and across species lines. Within the limit of resolution of agarose gels the length of restriction fragments formed by cleavage of two sites within the repeat unit (cleaved by the same enzyme or by combinations of enzymes) produces fragments of identical length. This indicates that the sequences separating the restriction sites are probably of identical or nearly identical sequence.

4. Specificity of the Repetitive Element

Southern blot hybridizations were performed with DNA from various strains of nontuberculous mycobacteria to confirm the specificity of the repeated sequence. When DNA of *M. avium*, *M. intracellulare*, *M. scrofulaceum*, *M. Kansasii*, *M. gordonae*, *M. fortuitum* or *M. chelonei* was digested with Sst11 or BamH1, enzymes which would produce single or multiple hybridizing fragments respectively, and hybridized with probes, pDC106 and pDC73, no hybridization was noted. The data confirm that the repeat is not present in the DNA of mycobacteria outside of the *M. tuberculosis* complex. These results suggest that the sequence appeared at a time after the *M. tuberculosis* complex diverged from other mycobacteria.

5. Fingerprinting of Genomic DNA

When genomic DNA of *M. tuberculosis* was restricted with enzymes for which there were no sites in the repeat, multiple fragments ranging in number from six to twelve were observed. Although we observed differences in patterns among strains, the fragments were too large to be well resolved on the gels. In order to produce smaller fragments and to increase their number, an enzyme with a single restriction site in the insertion sequence (BamH1) was chosen. Restriction with BamH1 produces fragments which extend from that site to BamH1 sites (left and right) in the DNA which flanks the repetitive element. The DNA extending from the conserved BamH1 site in the repeat to the proximal BamH1 in the DNA flanking the left end of the repeat can be detected by hybridization with the Sst11 fragment of pDC106 (see FIG. 1). DNA extending from the BamH1 fragment in the repeat to the BamH1 site in the DNA flanking the right end of the repeat can be detected by hybridization with the BamH1 - Sal1 fragment of pDC73 (FIG. 1).

Southern blots of BamH1 restricted DNA from *M. tuberculosis* H37Rv and the six clinical isolates demonstrate about 12 bands with each probe confirming that there are multiple copies of the repetitive segment. As expected, the banding patterns for each strain obtained with the two probes differ from one another. While some of the fragments from the various strains of *M. tuberculosis* DNA hybridized with the same probe appear to be the same, each strain has a pattern which is characteristic of that strain and differs from the others. Such differences are apparent in Southern blots hybridized with either probe. The patterns suggest a relatedness between H37Rv and clinical isolates T2 and T4 in contrast to clinical isolates T1 and T5 which differ strikingly. H37Rv and H37Ra Goldman, virulent and avirulent derivatives of H37, were also compared. Even these two closely related strains exhibit significant differences in restriction fragments.

Differences in restriction sites flanking the repetitive sequence are useful in characterizing the DNA of various *M. bovis* and *M. tuberculosis* strains. The inventors found BamH1 to be useful for this purpose, because the fragments produced are well resolved on agarose gels. Further, by using the two cloned fragments (the Sst11 fragment and the BamH1-Sal1 fragment), two sets of 10–12 bands can be demonstrated in a single digest. Other enzymes or combinations of enzymes may prove equally useful.

The use of the repetitive element in fingerprinting the DNA of individual strains should prove important in epidemiological studies. This approach is being applied to a number of bacterial pathogens. Owen, J. Med. Microbiol. 30: 89–99, 1989. In examining the DNA of only eight strains, no identical patterns were detected. Although the rate at which the sequences diverge in *M. tuberculosis* in unknown, it is contemplated that the fingerprint patterns will be relatively stable, and therefore useful in studying various isolates from specific outbreaks of tuberculosis. More importantly, these results suggest that as more fingerprint patterns are studied, it will be possible to divide *M. tuberculosis* strains into subgroups based on overall patterns rather than specific band differences. For example, H37Rv, H37Ra, strain T2 and T4 are not identical, but may represent a subgroup distinct from strains T1 and T5. These groupings may correlate with geographic origin, relative virulence or other variables.

EXAMPLE 3

(1) DNA Sequencing

DNA sequence analysis was conducted on a portion of the repetitive DNA segment from *Mycobacterium tuberculosis*. Mycobacterial DNA was isolated according to the procedure in Example 1. The concentration of DNA was determined by measuring the optical density at 260 nm. A single fragment of clone M13KE39 was obtained by partial digestion with endonuclease Sau 3A and subcloned into M13mp18 and M13mp19 for sequencing using the dideoxy chain termination technique. Both strands were sequenced. These subclones hybridized with the λKE55 and λKE58 clones described in Example 2.

A portion of the repetitive DNA segment from *M. tuberculosis* is illustrated in Table 2. As shown, the segment is comprised of 123 base-pairs and a 6 base-pair internal Sal1 site. This sequence is part of a larger repetitive segment. On the basis of the analysis of the sequence of M13KE39, it was predicted that there would be a Sal1 site located 55 bp from one end of the 123-bp amplified fragment. When the amplified fragment was digested with Sal1, it was cut into 2 fragments which measure approximately 50 and 70 nucleotides in length. This locates the Sal11 site at the expected distance from the BamH1 site in the repetitive sequence. The location of this specific sequence is shown on the restriction map of the repetitive element as illustrated in FIG. 2.

TABLE 2

| Sequence of the Repetitive DNA Segment from *Mycobacterium tuberculosis* | |
|---|---|
| <u>CCTGCGAGCG TAGGCGTCGG</u> TGACAAAGGC CACGTAGGCG AACCCTGCCC AGGTCGACAC | 60 |
| ATAGGTGAGG TCTGCTACCC ACAGCCGGTT AGGTGCTGGT GGT<u>CCGAAGC GGCGCTGGAC</u> | 120 |
| <u>GAG</u> | 123 |

The 20 base regions used for priming the reaction are underlined.

(2) Polymerase Chain Reactions

A portion of the repetitive DNA segment from *Mycobacterium tuberculosis* as shown in Table 2 was selected as a target for amplification using polymerase chain reaction (PCR).

Nucleotide primers were synthesized on a DNA synthesizer (Model 381A, Applied Biosystems, Foster City, Calif.) using B-cyanoethyl phosphoramidite chemistry. The DNA was deblocked using ammonium hydroxide and purified by passage through a Sephadex G-25 column (NAP-25, Pharmacia, Piscataway, N.J.), and ethanol precipitation. The sequences of the oligonucleotide primers were 5′-CCTGCGAGCGTAGGCGTCGG-3′ and 5′-CTCGTCCAGCGCCGCTTCGG-3′. Nucleotide primers corresponding to the indicated sequence were synthesized for use in PCR.

Amplification reactions were performed using *Thermus aquaticus* (Taq) polymerase and reagents according to the manufacturer's instructions (GeneAmp Kit; Perkin-Elmer Cetus). Buffer, nucleotides, primers (1 μM each), and enzymes were mixed and then dispensed in 45 μl aliquots. DNA was added in a volume of 5 μl, and the reaction mixture was overlayed with mineral oil. A control tube containing no DNA was included with each set of reactions.

The reaction was performed using an automated thermal cycler (DNA Thermal Cycler; Perkin-Elmer Cetus). The samples were denatured at 94° C. for five minutes. Twenty-five amplification cycles were performed. A cycle consisted of denaturation at 94° C. for two minutes, annealing of primers at 68° C. for two minutes, and primer extension at 72° C. for two minutes. The extension time was increased by 5 s with each subsequent cycle. The product was analyzed by electrophoresis on 0.8% agarose gels with 12% acrylamide gels. The DNA was stained with ethidium bromide and photographed on a 302-nm ultraviolet transilluminator.

Amplification of the sequence of the repetitive DNA segment from *M. tuberculosis* produces a 123 base-pair segment with a 6 base-pair internal site for endonuclease Sal1. An annealing temperature of 68° C. is necessary to produce the segment. The results further indicate that the primer segments have a 75% G+C content with the A and T residues well spaced, which allows for the use of a high primer annealing temperature. This contributes to the specificity of the reaction and may also increase the sensitivity of the reaction.

Although hybridization assays demonstrated the repetitive nature of the DNA sequence in *M. tuberculosis*, it was not known if each copy of the sequence was conserved or if each could be amplified using the oligonucleotide primers. To this end, DNA from *M. tuberculosis* strain T2 was digested with endonuclease BamH1, which does not cleave within the PCR target. Two aliquots containing 1.45 µg and 145 ng of DNA were electrophoresed. The lane containing 1.45 µg of DNA was transferred to a nylon membrane (GeneScreen Plus), using an alkaline procedure. Chomczynski, Biochem. Biophys. Res. Commun. 122: 340–344, 1984. That lane was further blotted and probed by hybridization with labeled PCR product, the 123 base-pair segment produced by the PCR reaction. The lane containing 145 ng of DNA was sliced into 28 fractions, melted, and then diluted 1000-fold in water. 5 µl aliquots of certain fractions were then amplified by PCR.

The results indicate that at least 12 copies of the sequence existed. Further, all of the individual copies were amplified using the same primers.

Next, the specificity of the PCR was determined. Accordingly, DNA from 39 strains of mycobacteria were assayed. Relatively high amounts of input DNA (625 pg per reaction) were used to ensure that an amplification would be detected.

DNA was amplified from 10 strains of *M. tuberculosis* and *M. bovis* and 1 strain of *M. simiae* to yield the 123 base-pair product. Also, when the amplification products were digested with Sal1, identical Sal1 fragments were obtained with these strains. On the other hand, no product was detected with the DNA from nontuberculosis mycobacteria (e.g., 28 strains of the *M. avium* complex, *M. kansasii, M. scrofulaceum, M. fortuitum, M. chelone;* and *M. gordonae*). Lack of amplification was confirmed by hybridization of a blot of the gel.

Finally, the sensitivity of detection of DNA by PCR was assessed. Ten-fold serial dilutions of *M. tuberculosis* strain T2 DNA were amplified. One set of samples was amplified for 25 cycles and another for 30 cycles. The PCR product was detected after 25 cycles from 100 fg of input DNA, while detection occurred after 30 cycles with only 1 fg of input DNA (or roughly equivalent to one copy of the *M. tuberculosis* chromosome). No product was detected after 30 cycles with *M. avium* DNA, human DNA alone, or in the control sample containing no input DNA.

These results demonstrate that amplification of the target DNA sequence in *M. tuberculosis* can provide a diagnostic approach for dramatically increasing the sensitivity of detection of the organism directly in clinical material. Although only one part of the entire repetitive DNA sequence was amplified, it is contemplated that any part of the entire sequence can be similarly used.

(3) Detection of *M. tuberculosis* in Sputum Samples Using PCR

Techniques were developed that enable the PCR to be applied directly to clinical samples. Procedures involved establishing a method for lysing mycobacteria, extracting the DNA, and testing for the presence of the 123-bp fragment by PCR. 162 sputum samples, half of which were smear positive for acid-fast bacilli, were tested using this technique.

(a) Patient samples. sputum samples were obtained from the Arkansas State Health Department laboratory where the specimens were treated with the standard protocol of n-acetylcysteine-NaOH. The sediments remaining after microscopy and inoculation of solid media were stored at 4° C. until they were processed for PCR.

(b) Specimen processing for PCR. Sediment from the sputum sample was centrifuged in a screw cap microfuge tube for 5 minutes. The pellet was suspended in TE buffer (10 mM Tris, pH 8.0, 1 mM EDTA) containing 20 mg/ml lysozyme and incubated at 37° C. for 2 hours. Subsequently, NaOH and sodium dodecyl sulfate were added to final concentrations of 0.5N and 1% respectively, and the tube was placed in a boiling water bath for 5 minutes. Once at room temperature the sample was neutralized with HCl. The DNA was extracted and concentrated by binding to powdered glass using the GeneClean kit (B10 101 Inc., La Jolla, Calif.). The DNA was eluted from the powdered glass in 10 ml of water.

(c) Controls. As a control for the lysis reagents and procedure, a tube containing $10^3$ *M. tuberculosis* organisms and a tube containing no organisms were processed in each batch of clinical samples. A positive control tube containing 100 pg of *M. tuberculosis* DNA and a negative control tube containing no DNA were included with each set of reactions. Control DNA that produces a 600-bp PCR product with the same primers was included in each reaction as an internal control. The control DNA was constructed as follows.

A single-stranded 46 nucleotide oligomer was synthesized which consists of the two, 20 base primer sequences with a 6 base EcoR1 restriction enzyme site in the middle. The DNA was synthesized by Bio-Synthesis, Inc. (Denton, Tex.) and was purified by polyacrylamide gel electrophoresis. The 46mer was amplified by PCR, and the double-stranded product was blunt-end ligated into the Sma1 site of a modified pUC 19 vector from which the EcoR1 site had been removed. DNA from the resulting clone was digested with EcoR1 and ligated with a 550-bp EcoR1 fragment of DNA isolated from *Salmonella typhimurium*. This clone, which contains a fragment of *S. typhimurium* DNA inserted between the primers, is referred to as pDC139.

(d) Results. For the clinical trial 162 sputum samples were processed for PCR testing according to the procedure previously described. Following amplification, the product was detected by acrylamide gel electrophoresis. Samples were determined to be PCR positive based on the visualization of a 123-bp fragment on the gel, and negative if a 123-bp fragment was absent. The 600-bp fragment of the internal control DNA was also present.

Of the 162 sputum samples tested, 82 were smear positive for acid-fast bacilli. Of the 94 specimens from patients diagnosed as having pulmonary tuberculosis, 51 were culture positive, smear positive, or both. Fifty of these tested PCR positive. Of the 42 specimens from patients with nontuberculosis mycobacterial disease, 41 tested PCR negative. All 26 specimens from patients without mycobacterial infection were PCR negative.

This assay provides a sensitive and specific means for the laboratory diagnosis of tuberculosis within a brief period of time (48 hours). Further, the assay is relatively simple to perform, providing additional benefits to health care institutions in their delivery of diagnostic services.

(4) Detecting *M. tuberculosis* in Sputum Samples Using a Probe Assay

A simple and efficient procedure for lysis of mycobacteria from sputum was developed for the application to a membrane-based hybridization assay. Initially, pure cultures of mycobacteria were used for testing the lysis procedure and subsequently processed sputum sediment was used. Optimum lysis was achieved with the following procedure.

A cell suspension or sputum sediment was centrifuged at 12,000×g for 5 minutes. The supernatant was decanted, and the cell pellet was resuspended in 500 μl TE buffer. 100 mg of zirconium beads (0.1 mm) was added, and the tube was agitated at high speed in a Minibead Beater (Biospec Products, Bartelsville, Okla.) for 3 minutes. The tube was then placed in a boiling water bath for 10 minutes to render the sample noninfectious. The sample was denatured by adding NaOH to the final concentration of 0.25N NaOH. The tube was centrifuged for 2 minutes to remove debris, and the entire sample was loaded on a membrane using a slot blotter apparatus. The membranes were hybridized and washed to remove unbound probe, according to the conditions as described in Example 1.

Using $^{32}$P-labeled pDC92 (described in Example 2), to probe the membranes, as few as $10^2$–$10^3$ mycobacterial cells per ml were detected. Since a limited number of smear positive and smear-negative sputum samples have been processed with this procedure, the sensitivity and specificity have not yet been determined.

The present invention involves the various embodiments associated with a composition comprising a repetitive segment of *Mycobacterium tuberculosis* DNA and its use in all respects, and is not to be construed as limited to any specific aspect or embodiment except as defined by the lawful scope of the appended claims.

We claim:

1. A composition used as target material for amplification by polymerase chain reaction, consisting of:
a repetitive DNA segment in the chromosome of *M. tuberculosis* that is specific for *M. tuberculosis* complex strains, wherein the segment consists of a 123 base-pair DNA (nucleotide) sequence:

CCTGCGAGCG TAGGCGTCGG TGACAAAGGC

CACGTAGGCG AACCCTGCCC AGGTCGACAC     60

ATAGGTGAGG TCTGCTACCC ACAGCCGGTT

AGGTGCTGGT GGTCCGAAGC GGCGCTGGAC     120

GAG                                                                  123.

2. The composition of claim 1, wherein the nucleotide primers for the DNA sequence consists of 5'-CCTGCGAGCGTAGGCGTCGG-3' and 5'-CTCGTCCAGCGCCGCTTCGG-3'.

3. The composition of claim 1, wherein the DNA sequence contains an internal site for endonuclease Sal1 consisting of: 5'-GTCGAC-3'.

4. The composition of claim 1, wherein amplification of the DNA segment produces a 123 base-pair product.

5. A method of diagnosing tuberculosis in clinical material, comprising the steps of:
amplifying a repetitive DNA segment of *Mycobacterium tuberculosis* that is specific for *M. tuberculosis* complex strains using polymerase chain reaction, wherein the segment consists of a 123 base-pair DNA (nucleotide) sequence:

CCTGCGAGCG TAGGCGTCGG TGACAAAGGC

CACGTAGGCG AACCCTGCCC AGGTCGACAC     60

ATAGGTGAGG TCTGCTACCC ACAGCCGGTT

AGGTGCTGGT GGTCCGAAGC GGCGCTGGAC     120

GAG; and                                                              123 detecting the presence of the 123 base-pair DNA sequence.

6. The method of claim 5, wherein the nucleotide primers for the DNA sequence consists of: 5'-CCTGCGAGCGTAGGCGTCGG-3' and 5'-CTCGTCCAGCGCCGCTTCGG-3'.

7. The method of claim 5, wherein the DNA sequence contains an internal site for endonuclease Sal1 Aconsisting of: 5'-GTCGAC-3'.

8. The method of claim 5, wherein amplification of the DNA segment produces a 123 base-pair product.

9. A method for directly detecting *Mycobacterium tuberculosis* in clinical samples using polymerase chain reaction, comprising the steps of:
(a) lysing mycobacteria in clinical samples;
(b) extracting the DNA of the mycobacteria;
(c) assaying the DNA for the presence of a DNA fragment by polymerase chain reaction, wherein the DNA fragment consists of a 123 base-pair DNA (nucleotide) sequence:

CCTGCGAGCG TAGGCGTCGG TGACAAAGGC

CACGTAGGCG AACCCTGCCC AGGTCGACAC     60

ATAGGTGAGG TCTGCTACCC ACAGCCGGTT

AGGTGCTGGT GGTCCGAAGC GGCGCTGGAC     120

GAG; and                                                              123

(d) detecting the presence of the 123 base-pair DNA sequence.

10. The method of claim 9, wherein the clinical samples are sputum samples.

11. The method of claim 9, wherein the nucleotide primers for the DNA sequence consists of: 5'-CCTGCGAGCGTAGGCGTCGG-3' and 5'-CTCGTCCAGCGCCGCTTCGG-3'.

12. A DNA segment, pDC139, for use as an internal control in polymerase chain reaction for the detection of *Mycobacterium tuberculosis* in clinical samples.

13. The DNA segment of claim 12, wherein amplification of the DNA segment produces an approximate 600-bp product.

14. The DNA segment of claim 12, wherein the nucleotide primers for the DNA segment consists of: 5'-CCTGCGAGCGTAGGCGTCGG-3' and 5'-CTCGTCCAGCGCCGCTTCGG-3'.

15. A method for confirming the amplification of DNA with polymerase chain reaction, comprising the steps of:
    (a) lysing microorganisms in clinical samples;
    (b) extracting the DNA of the microorganisms;
    (c) adding nucleotide primers to the samples of step (b);
    (d) adding a DNA segment, as an internal control, to the samples of step (c) which uses the nucleotide primers for amplification;
    (e) amplifying the microbial DNA and the internal control DNA segment by polymerase chain reaction; and
    (f) detecting the presence of at least one DNA fragment as defined by the nucleotide primers in step (c).

16. The method of claim 15, wherein the internal control DNA segment is pDC139.

17. The method of claim 15, wherein amplification of the internal control DNA segment produces approximately a 600-bp product.

18. The method of claim 15, wherein the nucleotide primers for the microbial DNA and the internal control DNA segment consists of: 5'-CCTGCGAGCGTAGGCGTCGG-3' and 5'-CTCGTCCAGCGCCGCTTCGG-3'.

19. The method of claim 15, wherein amplification of the microbial DNA produces a 123 base-pair product consisting of the DNA sequence:

<u>CCTGCGAGCG TAGGCGTCGG</u> TGACAAAGGC
CACGTAGGCG AACCCTGCCC AGGTCGACAC           60
ATAGGTGAGG TCTGCTACCC ACAGCCGGTT
AGGTGCTGGT GGT<u>CCGAAGC GGCGCTGGAC</u>          120
<u>GAG</u>                                        123.

* * * * *